(12) United States Patent
Liu

(10) Patent No.: US 8,013,007 B2
(45) Date of Patent: Sep. 6, 2011

(54) ALPHA 1A-ADRENOCEPTOR ANTAGONISTS

(75) Inventor: Julie F. Liu, Lexington, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 533 days.

(21) Appl. No.: 12/072,501

(22) Filed: Feb. 26, 2008

(65) Prior Publication Data

US 2009/0012112 A1 Jan. 8, 2009

Related U.S. Application Data

(60) Provisional application No. 60/903,472, filed on Feb. 26, 2007.

(51) Int. Cl.
*A61K 31/404* (2006.01)
*C07D 209/04* (2006.01)

(52) U.S. Cl. .................................... 514/415; 548/491

(58) Field of Classification Search .................. 514/415; 548/491
See application file for complete search history.

(56) References Cited

U.S. PATENT DOCUMENTS

| | | | |
|---|---|---|---|
| 5,387,603 A * | 2/1995 | Kitazawa et al. ............. | 514/415 |
| 5,403,847 A | 4/1995 | Gluchowski et al. | |
| 5,780,485 A | 7/1998 | Gluchowski et al. | |
| 6,015,819 A | 1/2000 | Gluchowski et al. | |
| 6,054,455 A * | 4/2000 | Guess et al. ............... | 514/231.2 |
| 6,221,335 B1 | 4/2001 | Foster | |
| 6,310,086 B1 | 10/2001 | Kitazawa et al. | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 2004/0132697 A1 | 7/2004 | Thurlow et al. | |
| 2005/0080056 A1 | 4/2005 | Horn | |
| 2006/0142374 A1 | 6/2006 | Tsuru et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |
| 2010/0076010 A1 * | 3/2010 | Liu .............................. | 514/284 |

FOREIGN PATENT DOCUMENTS

| | | |
|---|---|---|
| JP | 07-330726 | 12/1995 |
| JP | 2006-188470 | 7/2006 |
| WO | WO 95/26325 | 10/1995 |
| WO | WO 2005/089742 A1 | 9/2005 |
| WO | WO 2006/046499 A1 | 5/2006 |
| WO | WO 2007/118651 A1 | 10/2007 |
| WO | WO 2008/106125 A2 | 9/2008 |

OTHER PUBLICATIONS

Kawabe et al. "Silodosin, a new α1A-adrenoceptor-selective antagonist for treating benign prostatic hyperplasia: results of a phase III randomized, placebo-controlled, double-blind study in Japanese men" BJU International, 2006, vol. 98, No. 5, pp. 1019-1024.*
Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).
Kushner, D.J. et al., "Pharmacological Uses and Perspectives of Heavy Water and Deuterated Compounds," Can. J. Physiol. Pharmacol., 77:79-88 (1999).
Murata S., et al., "Pharmacological Analysis of the Novel, Selective α1-Adrenoceptor Antagonist, KMD-3213, and its Suitability as a Tritiated Radioligand," Br. J. Pharmacol., 127:19-26 (1999).
Vatz, K.A., "Alpha 1-Adrenergic Blockers: Do They Have a Place in the Prophylaxis of Migraine?," Headache, 37(2):107-108 (1997).
Product Insert and Label for Rapaflo™ (silodosin), Watson Pharmaceuticals, Inc., 31 pgs. (2008).
International Search Report, International Application No. PCT/US2008/002513, Aug. 18, 2008.
Written Opinion of the International Searching Authority, International Application No. PCT/US2008/002513, Aug. 18, 2008.
English Language Abstract for JP Publication No. 07-330726 (B2) retrieved from the Industrial Property Digital Library of the Japanese Patent Office website as Patent Abstracts of Japan on Jun. 11, 2009.
English Language Abstract for JP Publication No. 2006-188470 (B5) retrieved from the Industrial Property Digital Library of the Japanese Patent Office website as Patent Abstracts of Japan on Jun. 11, 2009.
Baillie, Thomas A., "The Use of Stable Isotopes in Pharmacological Research", Pharmacological Reviews, vol. 33, No. 2, pp. 81-132, 1981.
Browne, Thomas R., "Stable Isotope Techniques in Early Drug Development: An Economic Evaluation", J. Clin. Pharmacol, vol. 38, pp. 213-220, 1998.
Cherrah, et al., "Study of Deuterium Isotope Effects on Protein Binding by Gas Chromatography/Mass Spectrometry. Caffeine and Deuterated Isotopomers", Biomedical and Environmental Mass Spectrometry, vol. 14, pp. 653-657, 1987.
Dyck, et al., "Effects of Deuterium Substitution on the Catabolism of β-Phenylethylamine: An In Vivo Study", Journal of Neurochemistry, vol. 46, No. 2, pp. 399-404, 1986.
Foster, Allan B., "Deuterium isotope effects in studies of drug metabolism", TIPS, pp. 524-527, Dec. 1984. Foster, Allan B., "Deuterium isotope effects in the metabolism of drugs and xenobiotics", Advances in Drug Research vol. 14, pp. 2-40, 1985.
Gouyette, et al., "Synthesis of Deuterium-labelled Elliptinium and its Use in Metabolic Studies", Biomedical and Environmental Mass Spectrometry, vol. 15, pp. 243-247, 1988.
Haskins, N.J., "The Application of Stable Isotopes in Biomedical Research", Biomedical Mass Spectrometry, vol. 9, No. 7, pp. 269-277, 1982.
Honma, et al., "Liberation of Deuterium from the Piperidine Ring during Hydroxylation", Drug Metabolism and Disposition, vol. 15, No. 4, pp. 551-559, 1987.
Matsubara, et al., "Pharmacokinetics and Disposition of Silodosin (KMD-3213)", Yakugaku Zasshi, vol. 126, pp. 237-245, 2006.
Pieniaszek, et al., "Moricizine Bioavailablity via Simultaneous, Dual, Stable Isotope Administration: Bioequivalence Implications", The Journal of Clinical Pharmacology, vol. 39, pp. 817-825, 1999.
Tonn, et al., "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes", Biological Mass Spectrometry, vol. 22, pp. 633-642, 1993.
Wolen, Robert L., "The Application of Stable Isotopes to Studies of Drug Bioabailablity and Bioequivalence", The Journal of Clinical Pharmacology, vol. 26, pp. 419-424, 1986.

* cited by examiner

Primary Examiner — Joseph Kosack
(74) Attorney, Agent, or Firm — McCarter & English LLP; Steven G. Davis

(57) ABSTRACT

This invention relates to novel compounds that are dihydroindoles derivatives and pharmaceutically acceptable salts thereof. More specifically, this invention relates to novel dihydroindoles derivatives that are derivatives of silodosin. This invention also provides compositions comprising one or more compounds of this invention and a carrier and the use of the disclosed compounds and compositions in methods of treating diseases and conditions that are beneficially treated by administering an α-1A-adrenoreceptor antagonist, such as silodosin.

30 Claims, No Drawings

ALPHA 1A-ADRENOCEPTOR ANTAGONISTS

RELATED APPLICATION

This application claims the benefit of U.S. Provisional Application No. 60/903,472, filed on Feb. 26, 2007. The entire teachings of the above application is incorporated herein by reference.

BACKGROUND OF THE INVENTION

Silodosin is also known as (−)-1-(3-Hydroxypropyl)-5-[2(R)-[2-[2-(2,2,2-trifluoroethoxy)phenoxy]ethylamino]propyl]-2,3-dihydroindole-7-carboxamide; (R)-1-(3-hydroxypropyl)-5-(2-(2-(2-(2,2,2-trifluoroethoxy)phenoxy)ethylamino)-propyl)indoline-7-carboxamide; KAD-3213; and KMD-3213. It is marketed in Japan under the tradename URIEF® for the treatment of Lower Urinary Tract Symptoms (LUTS) associated with Benign Prostatic Hyperplasia (BPH).

Silodosin is currently in Phase III trials in the United States for the treatment of BPH.

Despite the beneficial activities of silodosin, there is a continuing need for new compounds to treat the aforementioned diseases and conditions.

SUMMARY OF THE INVENTION

This invention relates to novel compounds that are dihydroindoles derivatives and pharmaceutically acceptable salts thereof. More specifically, this invention relates to novel dihydroindoles derivatives that are derivatives of silodosin. This invention also provides compositions comprising one or more compounds of this invention and a carrier and the use of the disclosed compounds and compositions in methods of treating diseases and conditions that are beneficially treated by administering an α-1A-adrenoreceptor antagonist, such as silodosin.

DETAILED DESCRIPTION OF THE INVENTION

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of silodosin will inherently contain small amounts of deuterated and/or $^{13}C$-containing isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725.

The compounds of the present invention are distinguished from such naturally occurring minor forms in that the term "compound" as used in this invention refers to a composition of matter that has a minimum isotopic enrichment factor of at least 500 (7.5% deuterium incorporation) for each deuterium atom that is present at a site designated as a site of deuteration in Formula (I).

In the compounds of the invention, any atom not specifically designated as a particular isotope is meant to represent any stable isotope of that atom unless otherwise stated. Unless otherwise stated, when a position is designated specifically as "H" or "hydrogen," the position is understood to have hydrogen at its natural abundance isotopic composition.

The term "isotopic enrichment factor" as used herein means the ratio between the isotopic abundance (e.g., D or $^{13}C$) at a specified position in a compound of this invention and the naturally occurring abundance of that isotope. The natural abundance of deuterium is 0.015%. The natural abundance of $^{13}C$ is 1.11%.

In other embodiments, a compound of this invention has an isotopic enrichment factor for each deuterium present at a site designated as a potential site of deuteration on the compound of at least 1000 (15% deuterium incorporation), at least 1500 (22.5% deuterium incorporation), at least 2000 (30% deuterium incorporation), at least 2500 (37.5% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 22.5% while the other could be deuterated at 37.5% and still be considered a compound wherein the isotopic enrichment factor is at least 1500 (22.5%).

The structural formula depicted herein may or may not indicate whether atoms at certain positions are isotopically enriched. In a most general embodiment, when a structural formula is silent with respect to whether a particular position is isotopically enriched, it is to be understood that the stable isotopes at the particular position are present at natural abundance, or, alternatively, that that particular position is isotopically enriched with one or more naturally occurring stable isotopes. In a more specific embodiment, the stable isotopes are present at natural abundance at all positions in a compound not specifically designated as being isotopically enriched.

The term "isotopologue" refers to a species that differs from a specific compound of this invention only in the isotopic composition thereof. Isotopologues can differ in the level of isotopic enrichment at one or more positions and/or in the positions(s) of isotopic enrichment.

The term "compound," as used herein, is also intended to include solvates or hydrates thereof.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

"Tert", "t", and "t-" each refer to tertiary.

"US" refers to the United States of America.

"FDA" refers to Food and Drug Administration.

"NDA" refers to New Drug Application.

Throughout this specification, a variable may be referred to generally (e.g., "each R"), to encompass two related variables (e.g., "each $R^1$" to mean $R^{1a}$ and $R^{1b}$), or may be referred to specifically (e.g., $R^{1a}$, $R^{1b}$, $R^{2a}$, etc.). Unless otherwise indicated, when a variable is referred to generally, it is meant to include all specific embodiments of that particular variable.

Therapeutic Compounds

The present invention provides a compound of Formula I:

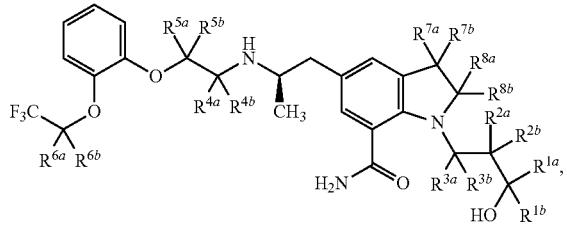

or a salt thereof,
wherein each R is independently selected from hydrogen or deuterium and at least one R is deuterium.

In one embodiment, each pair of R groups bound to a common atom are the same (i.e., they are either both hydrogen or both deuterium), and is selected independently from any other pair of R groups. For example, in such an embodiment, if $R^{1a}$ and $R^{1b}$ are hydrogen, the identity of each other pair (e.g., $R^{2a}$ and $R^{2b}$; $R^{3a}$ and $R^{3b}$; $R^{4a}$ and $R^{4b}$; and so on) is independently selected from hydrogen or deuterium.

In another embodiment, $R^{1a}$ and $R^{1b}$ are the same. In another embodiment, $R^{1a}$ and $R^{1b}$ are simultaneously deuterium.

In another embodiment, $R^{3a}$ and $R^{3b}$ are the same. In another embodiment, $R^{3a}$ and $R^{3b}$ are simultaneously deuterium.

In another embodiment, $R^{1a}$ and $R^{1b}$ are simultaneously deuterium; and $R^{3a}$ and $R^{3b}$ are the same. In another embodiment, $R^{1a}$, $R^{1b}$, $R^{3a}$ and $R^{3b}$ are simultaneously deuterium.

In another embodiment, $R^{1a}$, $R^{1b}$, $R^{3a}$ and $R^{3b}$ are simultaneously deuterium; and $R^{2a}$ and $R^{2b}$ are the same. In another embodiment, $R^{1a}$, $R^{1b}$, $R^{2a}$, $R^{2b}$, $R^{3a}$ and $R^{3b}$ are simultaneously deuterium.

In another embodiment, $R^{4a}$ and $R^{4b}$ are the same. In another embodiment $R^{4a}$ and $R^{4b}$ are simultaneously deuterium.

In another embodiment, $R^{5a}$ and $R^{5b}$ are the same. In another embodiment $R^{5a}$ and $R^{5b}$ are simultaneously deuterium.

In another embodiment, at least one pair of: $R^{4a}$ and $R^{4b}$, or $R^{5a}$ and $R^{5b}$ are simultaneously deuterium.

In another embodiment, $R^{6a}$ and $R^{6b}$ are the same. In another embodiment $R^{6a}$ and $R^{6b}$ are simultaneously deuterium.

In another embodiment, $R^{7a}$ and $R^{7b}$ are the same. In another embodiment $R^{7a}$ and $R^{7b}$ are simultaneously deuterium.

In another embodiment, $R^{8a}$ and $R^{8b}$ are the same. In another embodiment $R^{8a}$ and $R^{8b}$ are simultaneously deuterium.

In another embodiment, $R^{1a}$, $R^{1b}$, $R^{4a}$ and $R^{4b}$ are simultaneously deuterium.

In another embodiment, $R^{3a}$, $R^{3b}$, $R^{4a}$ and $R^{4b}$ are simultaneously deuterium.

In another embodiment, $R^{1a}$, $R^{1b}$, $R^{3a}$, $R^{3b}$, $R^{4b}$ are simultaneously In another embodiment, $R^{1a}$, $R^{1b}$, $R^{3a}$, $R^{3b}$, $R^{4a}$ and $R^{4b}$ are simultaneously deuterium.

In another embodiment, $R^{7a}$, $R^{7b}$, $R^{8a}$ and $R^{8b}$ are simultaneously deuterium.

In another embodiment, $R^{4a}$, $R^{4b}$, $R^{5a}$, $R^{5b}$, $R^{6a}$ and $R^{6b}$ are simultaneously deuterium.

In another embodiment, $R^{1a}$, $R^{1b}$, $R^{7a}$, $R^{7b}$, $R^{8a}$ and $R^{8b}$ are simultaneously deuterium.

In another embodiment, $R^{1a}$, $R^{1b}$, $R^{2a}$, $R^{2b}$, $R^{3a}$, $R^{3b}$, $R^{7a}$, $R^{7b}$, $R^{8a}$ and $R^{8b}$ are simultaneously deuterium.

In another embodiment, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$ and $R^{6b}$ are simultaneously deuterium.

In another embodiment each R is deuterium.

In yet another embodiment, the compound is selected from any one of the compounds (Cmpd) set forth in Table 1 (below):

TABLE 1

Exemplary Embodiments of Formula I

| Cmpd | each $R^1$ | each $R^2$ | each $R^3$ | each $R^4$ | each $R^5$ | each $R^6$ | each $R^7$ | each $R^8$ |
|---|---|---|---|---|---|---|---|---|
| 100 | D | D | D | D | D | D | D | D |
| 101 | D | H | H | H | H | H | H | H |
| 102 | D | H | H | D | H | H | H | H |
| 103 | D | H | D | H | H | H | H | H |
| 104 | H | H | H | D | H | H | H | H |
| 105 | H | H | D | D | H | H | H | H |
| 106 | D | H | D | H | H | H | H | H |
| 107 | D | H | D | D | H | H | H | H |
| 108 | D | D | D | D | D | D | H | H |
| 109 | H | H | H | H | H | H | D | D |
| 110 | H | H | H | D | D | D | H | H |
| 111 | D | D | D | H | H | H | H | H |
| 112 | D | D | D | H | H | H | D | D |
| 113 | D | H | H | H | H | H | D | D |

In another set of embodiments, any atom not designated as deuterium in any of the embodiments set forth above is present at its natural isotopic abundance.

The invention also provides intermediates useful in the preparation of the compounds of Formula (I). As such, the invention provides compounds represented by structural formula (XV):

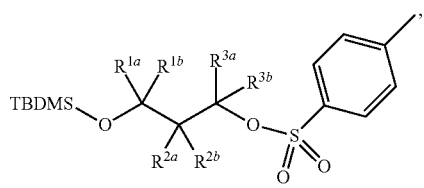

XV or a salt thereof, wherein each R is independently selected from hydrogen or deuterium and at least one R is deuterium.

In one embodiment, each pair of R groups bound to a common atom are the same (i.e., they are either both hydrogen or both deuterium), and is selected independently from any other pair of R groups.

In another embodiment, $R^{1a}$ and $R^{1b}$ are the same. In another embodiment, $R^{1a}$ and $R^{1b}$ are simultaneously deuterium.

In another embodiment, $R^{3a}$ and $R^{3b}$ are the same. In another embodiment, $R^{3a}$ and $R^{3b}$ are simultaneously deuterium.

In another embodiment, $R^{1a}$ and $R^{1b}$ are simultaneously deuterium; and $R^{3a}$ and $R^{3b}$ are the same. In another embodiment, $R^{1a}$, $R^{1b}$, $R^{3a}$ and $R^{3b}$ are simultaneously deuterium.

In another embodiment, $R^{1a}$, $R^{1b}$, $R^{3a}$ and $R^{3b}$ are simultaneously deuterium; and $R^{2a}$ and $R^{2b}$ are the same. In another embodiment, $R^{1a}$, $R^{1b}$, $R^{2a}$, $R^{2b}$, $R^{3a}$ and $R^{3b}$ are simultaneously deuterium.

In still another embodiment, in any of the aforementioned embodiments each atom not designated as deuterium is present at its natural isotopic abundance.

The invention provides compounds represented by Structural Formula IX:

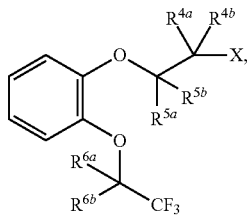

IX or a salt thereof, wherein each R is independently selected from hydrogen or deuterium and at least one R is deuterium; and X is selected from chlorine, bromine or iodine.

In one embodiment, each pair of R groups bound to a common atom are the same (i.e., they are either both hydrogen or both deuterium), and is selected independently from any other pair of R groups.

In another embodiment, $R^{4a}$ and $R^{4b}$ are the same. In another embodiment $R^{4a}$ and $R^{4b}$ are simultaneously deuterium.

In another embodiment, $R^{5a}$ and $R^{5b}$ are the same. In another embodiment $R^{5a}$ and $R^{5b}$ are simultaneously deuterium.

In another embodiment, at least one pair of: $R^{4a}$ and $R^{4b}$, or $R^{5a}$ and $R^{5b}$ are simultaneously deuterium.

In another embodiment, $R^{6a}$ and $R^{6b}$ are the same. In another embodiment $R^{6a}$ and $R^{6b}$ are simultaneously deuterium.

In another embodiment, $R^{4a}$, $R^{4b}$, $R^{5a}$, $R^{5b}$, $R^{6a}$ and $R^{6b}$ are simultaneously deuterium.

In yet another embodiment, in any of the aforementioned embodiments each R not designated as deuterium is hydrogen present at its natural isotopic abundance.

In still another embodiment, in any of the aforementioned embodiments each atom not designated as deuterium is present at its natural isotopic abundance.

The invention provides compounds represented by Structural Formula IA:

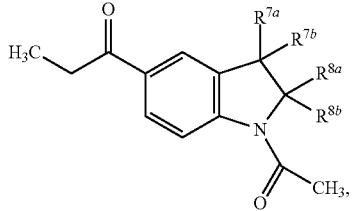

or a salt thereof, wherein each R is independently selected from hydrogen or deuterium; and at least one R is deuterium.

In one embodiment, each pair of R groups bound to a common atom are the same (i.e., they are either both hydrogen or both deuterium), and is selected independently from any other pair of R groups.

In another embodiment, $R^{7a}$ and $R^{7b}$ are the same. In another embodiment $R^{7a}$ and $R^{7b}$ are simultaneously deuterium.

In another embodiment, $R^{8a}$ and $R^{8b}$ are the same. In another embodiment $R^{8a}$ and $R^{8b}$ are simultaneously deuterium.

In another embodiment, $R^{7a}$, $R^{7b}$, $R^{8a}$ and $R^{8b}$ are simultaneously deuterium.

The synthesis of compounds of Formula I can be readily achieved by synthetic chemists of ordinary skill. Relevant procedures and intermediates are disclosed, for instance in U.S. Pat. No. 5,387,603.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A method for synthesizing compounds of Formula I is depicted in Scheme 1.

Scheme 1: Deuterated Derivatives Of Silodosin

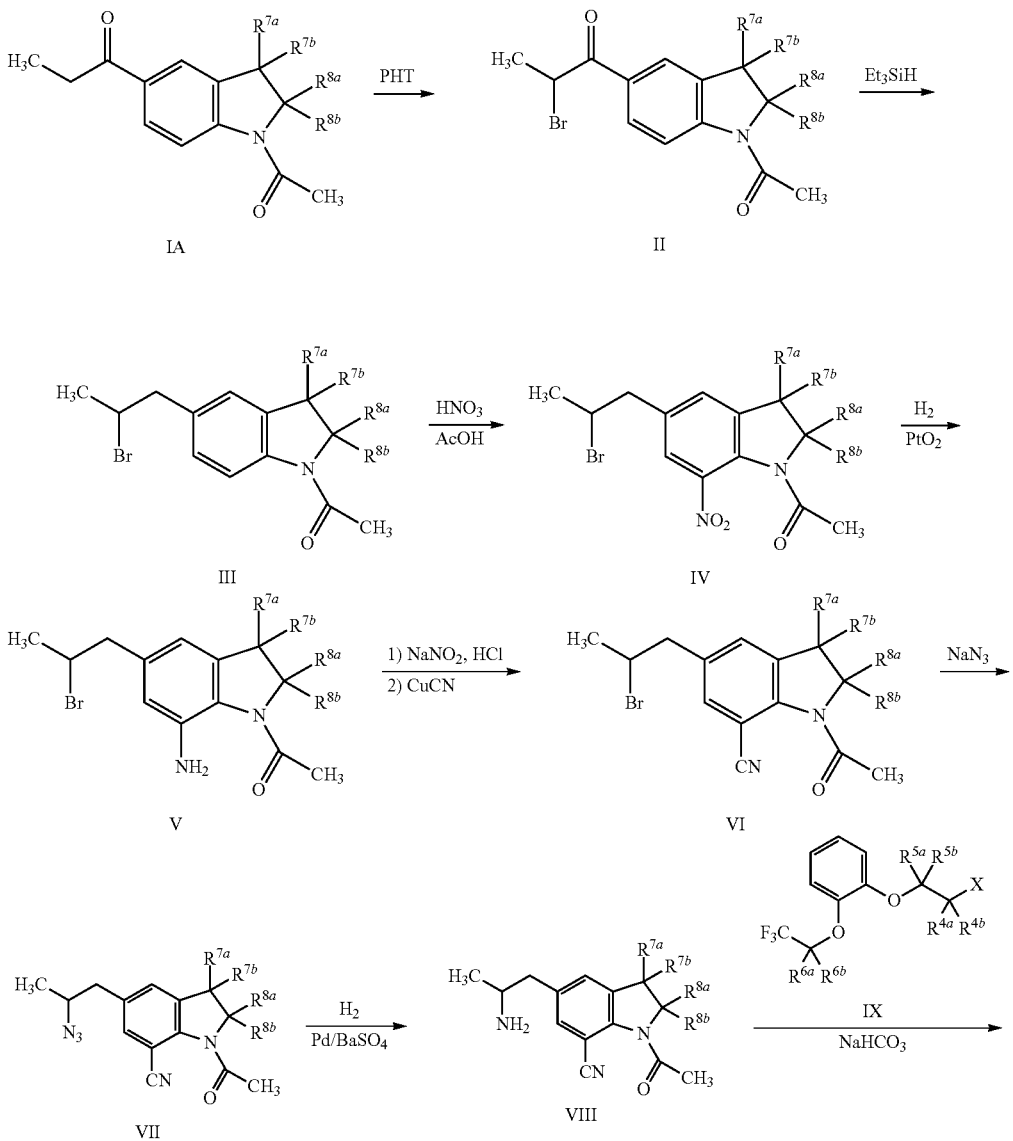

-continued
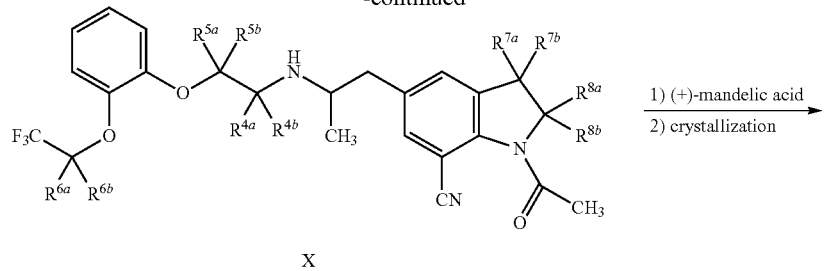
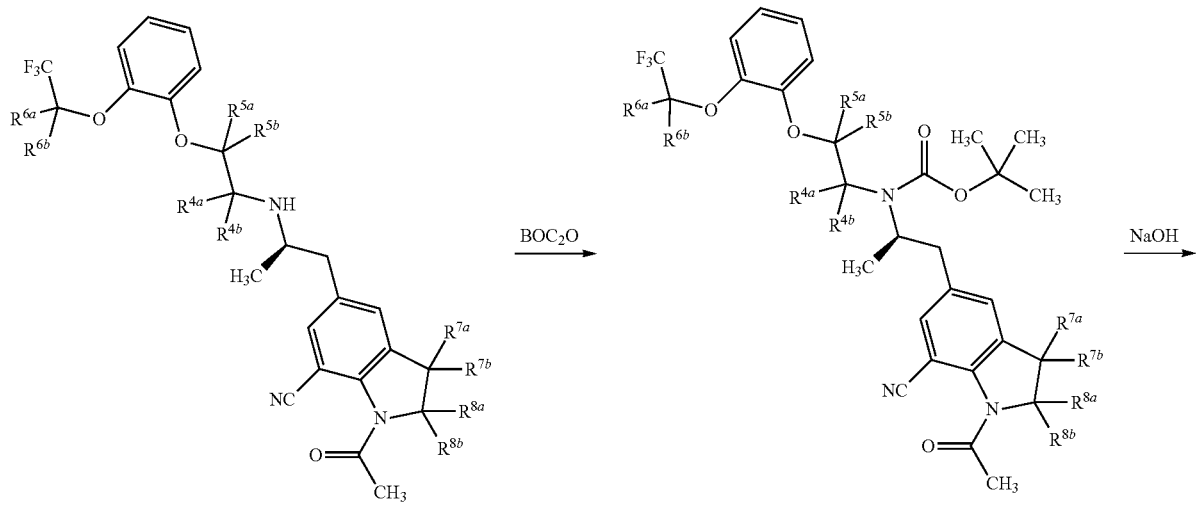
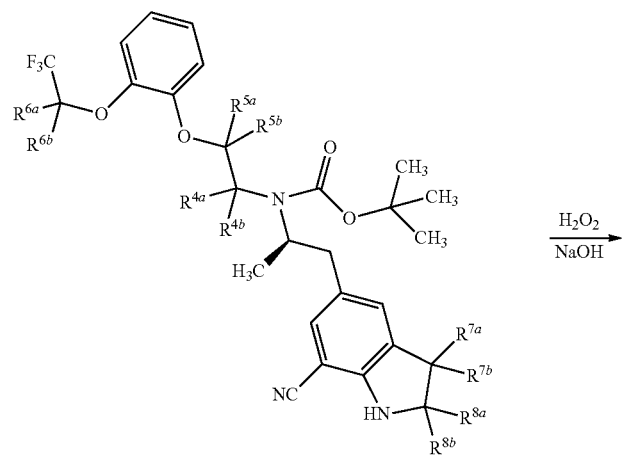

-continued
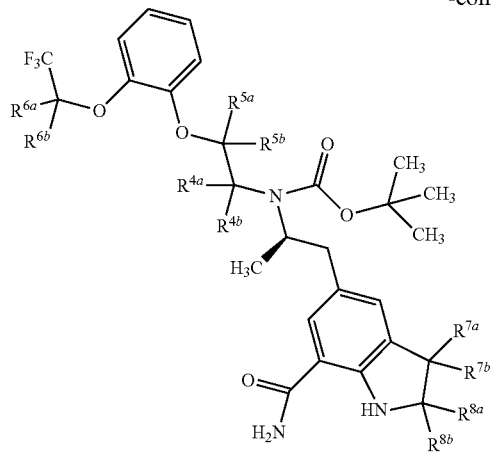
XIV
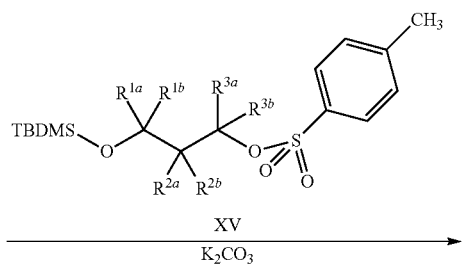
XV
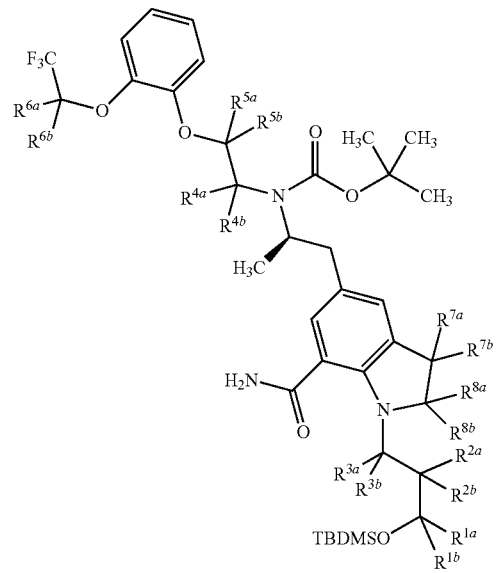
XVI
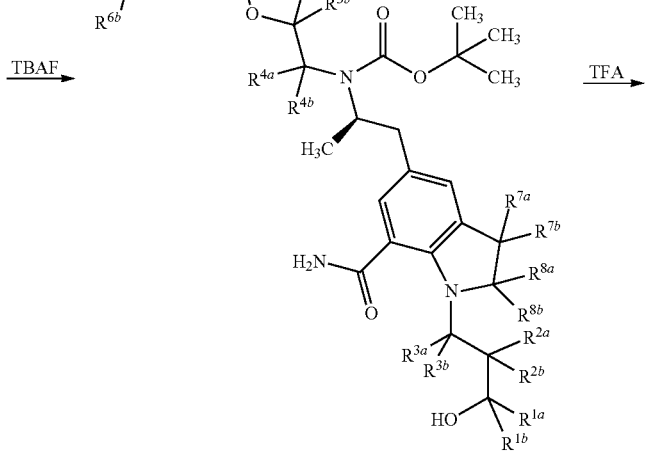
XVII
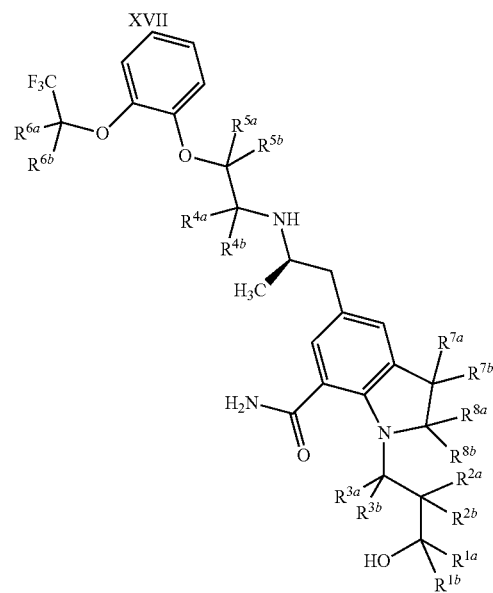
Formula I As provided in Scheme 1, the bromination of appropriately deuterated indoline IA with pyrrolidone hydrogen tribromide (PHT) and sulfuric acid in THF gives the alpha-bromo derivative II, which is reduced with triethylsilane in TFA yielding the 2-bromopropyl compound III. Nitration of III with HNO$_3$ in HOAc affords the 7-nitroindoline IV, which is reduced to the corresponding amine derivative V with H$_2$ over PtO$_2$ in ethanol. The reaction of amine V with NaNO$_2$/HCl, followed by treatment with CuCN, provides carbonitrile VI, which is treated with NaN$_3$ in hot ethylene glycol monomethyl ether/water to yield the 2-azidopropyl derivative VII. Reduction of VII with H$_2$ over Pd/BaSO$_4$ in ethanol affords the 2-aminopropyl VIII, which is condensed with the appropriately deuterated alkyl halide IX by means of NaHCO$_3$ in ethanol to provide the secondary amine X.

The optical resolution of amine X can be performed by treatment with (+)-mandelic acid in ethanol, followed by crystallization of the resulting salt and then treatment with Na$_2$CO$_3$ to afford the desired (R)-enantiomer XI. Compound XI is protected with Boc$_2$O to give the corresponding carbamate XII, which is deacetylated with NaOH in ethanol to yield the intermediate XIII. Hydrolysis of the cyano group of XIII with NaOH and H$_2$O$_2$ in DMSO furnishes the corresponding carboxamide XIV, which is condensed with the appropriate tosylate XV by means of K$_2$CO$_3$ and a crown ether in dioxane to provide the indoline adduct XVI. Finally, desilylation of XVI with TBAF in THF yields the 3-hydroxypropyl derivative XVII, which by removal of the Boc-protecting group by means of TFA in dichloromethane gives the desired final compound.

Scheme 2: Synthesis of Reagent IX.

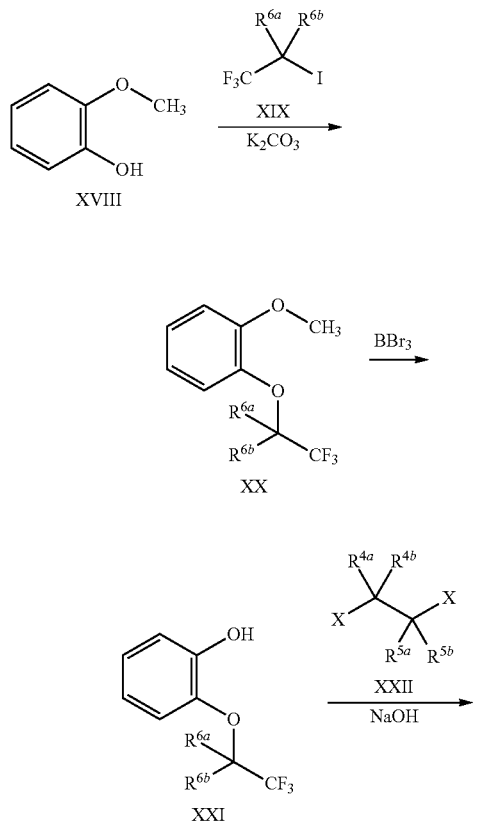

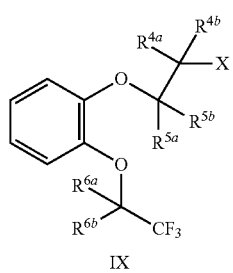

(X = independently Cl, Br, or I)

The intermediate alkyl halide IX may be obtained as depicted in Scheme 2 above. One skilled in the art will appreciate that X may also comprise OSO$_2$C$_6$H$_4$CH$_3$, OSO$_2$CH$_3$, OSO$_2$CF$_3$ instead of a halide. Thus, alkylation of 2-methoxyphenol XVIII with an appropriately-deuterated alkyl iodide XIX by means of K$_2$CO$_3$ in hot DMF gives phenyl ether XX, which is demethylated by means of BBr$_3$ in dichloromethane to yield the corresponding phenol XXI. Finally, this compound is alkylated with the appropriately-deuterated halide XXII and NaOH in water at 120° C.

Scheme 3: Synthesis of Reagent XV

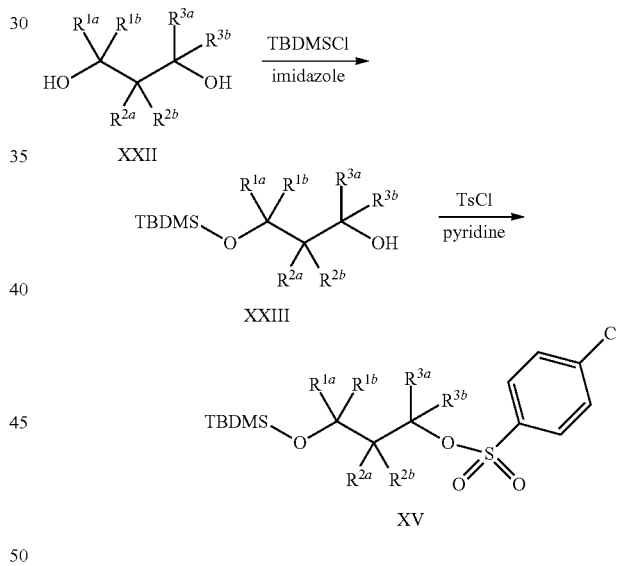

Reagent XV can be prepared as depicted in Scheme 3, above. Thus, the appropriately deuterated diol XXII is treated with imidazole and TBDMS chloride to product silyl ether XXIII, which is stirred with tosyl chloride and pyridine to provide desired tosylate XV.

Scheme 4: Starting Material IA

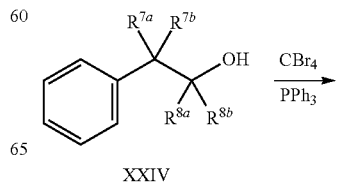

An alternative method for synthesizing compounds of Formula I is depicted in Scheme 5.

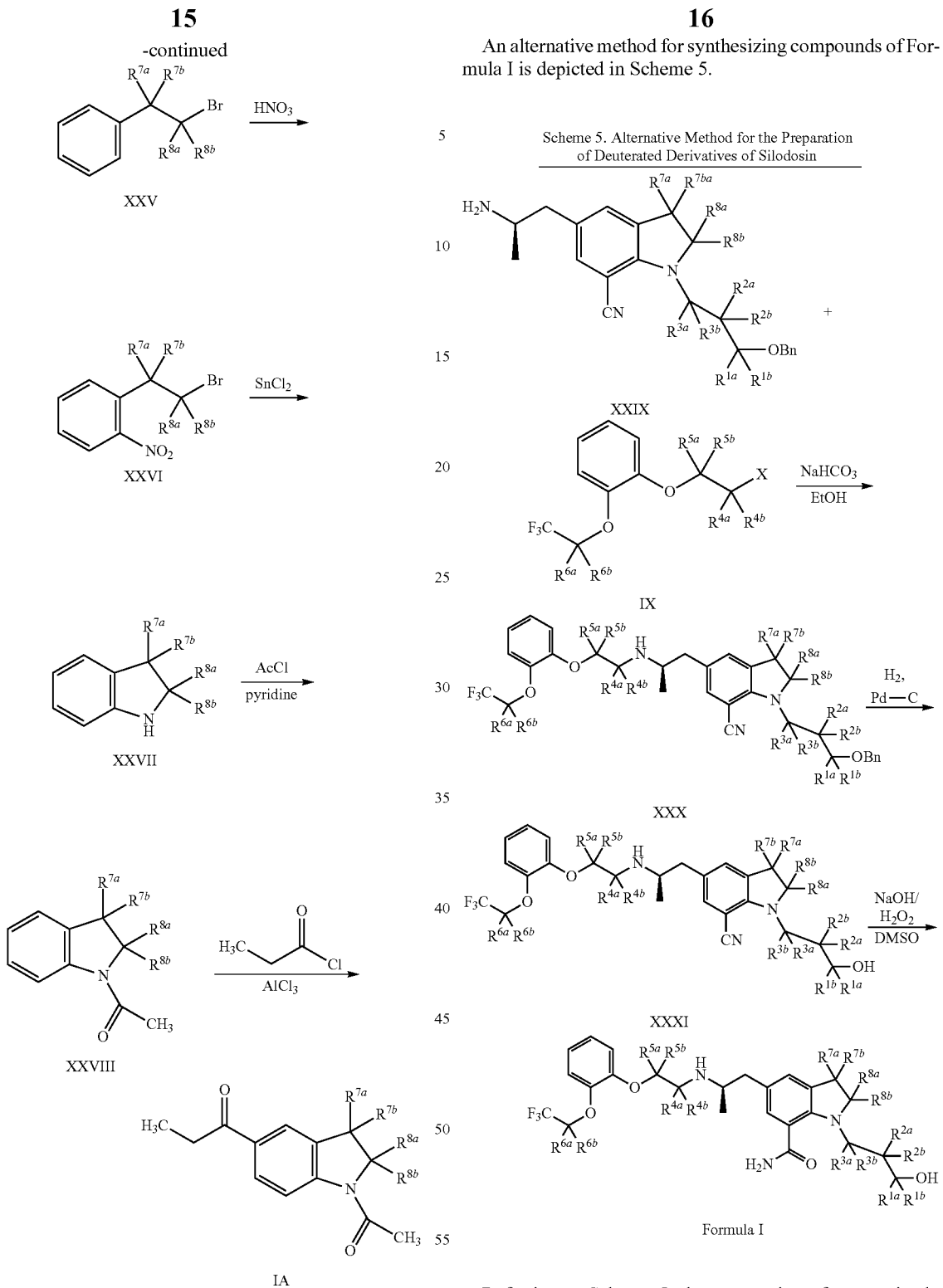

Starting Material IA can be prepared as depicted in Scheme 4, above. Thus, the appropriately deuterated alcohol XXIV is converted to bromide XXV with CBr$_4$ and PPh$_3$. Bromide XXV is treated with HNO$_3$ to produce nitroaryl XXVI, which is treated with SnCl$_2$ to produce dihydroindole XXVII. N-Acylation with acetyl chloride in pyridine provides amide XXVIII which is treated with AlCl$_3$ and EtC(O)Cl to provide desired starting compound IA.

Referring to Scheme 5, the preparation of appropriately deuterated amine XXIX can be carried out according to the procedure outlined in Japanese patent, JP 2006188470. As an additional matter, appropriately-deuterated amine XXIX can be prepared following JP 2006188470 using correspondingly deuterated reagents and starting materials. Amine XXIX is condensed with appropriately deuterated IX (where X=Br, Cl, I, OMs, OTf, or OTs) by means of NaHCO$_3$ in ethanol to provide the secondary amine XXX which is hydrogenated over Pd/C to afford the alcohol XXXI. Hydrolysis of the nitrile moiety of XXXI to the amide with NaOH/H$_2$O$_2$ in DMSO provides the desired final compound.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as silodosin. Such agents include those indicated as being useful in combination with silodosin, including but not limited to, those described in U.S. Pat. Nos. 6,235,759, 6,228,870 and 6,323,372; US Patent publications Nos US 20050101607, US 20040132728, US 20030225079; published International Application WO 2005/089804; and Canadian Published Application No. 2559646.

Preferably, the second therapeutic agent is an agent useful in the treatment or prevention of BPH.

In one embodiment, the second therapeutic agent is selected from 5-alpha reductase inhibitors (e.g., finasteride (PROSCAR®) and dutasteride (AVODART®)), HMG-CoA reductase inhibitors (e.g., atorvastatin (LIPITOR®), lovastatin (MEVACOR®), simvastatin (ZOCOR®) fluvastatin (LESCOL®), pravastatin (PRAVACHOL®) and rosuvastatin (CRESTOR®)), EGF-receptor antagonists, and beta-3-adrenoceptor antagonists.

In a particular embodiment, the second agent is a 5-alpha-reductase inhibitor. In more particular embodiment, the agent is selected from finasteride and dutasteride. In a most particular embodiment, the second therapeutic agent is finasteride.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.05 mg/day to about 500 mg/day, for example 0.05 mg/day to about 100 mg/day. Administration can be in one or more doses per day (e.g., multiple doses). When multiple doses are used, the amount of each dose can be the same or different.

In a particular embodiment, an effective amount of a compound of this invention can range from 0.8 mg/day to about 80 mg/day, such as from about 0.8 mg/day to about 40 mg/day. In a more particular embodiment, an effective amount of a compound of this invention can range from about 1.6 mg/day to about 20 mg/day. For example, an effective amount can be about 0.8 mg/day, about 1.0 mg/day, about 1.2 mg/day, about 1.4 mg/day, about 1.6 mg/day, about 1.8 mg/day, about 2 mg/day, about 3 mg/day, about 4 mg/day or about 8 mg/day. In a most particular embodiment, an effective amount is 8 mg/day administered either in a single dose (once a day) or in two doses per day. It is preferred, that when an effective amount is 8 mg/day and dosing is twice a day that the amount in each dose is 4 mg.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for silodosin.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of increasing the activity of the alpha (1A)-adrenoceptor in a cell, comprising contacting a cell with one or more compounds of Formula I herein.

According to another embodiment, the invention provides a method of treating a disease in a patient in need thereof that is beneficially treated by silodosin comprising the step of administering to said patient an effective amount of a compound or a composition of this invention. Such diseases include, but are not limited to, benign prostate hyperplasia (BPH); high intraocular pressure; high cholesterol; impotency; female sexual dysfunction (FSD) (e.g, female sexual arousal disorder (FSAD) and female orgasmic disorder (FOD), see U.S. Patent Application Publication 20040132697 to Thurlow et al.); sympathetically mediated pain; cardiac arrhythmia; and migraine (see Vatz, Headache (1997), 37: 107-108). The compounds and compositions of the invention can also be used in a method of modulating pupil dilation in subjects in need thereof (see U.S. Patent Application Publication 20050080056 to Horn et al.). Such modulation of pupil dilation can, for example, be used to improved vision of a subject in reduced lighting conditions by reducing excessive pupil dilation.

In one particular embodiment, the method of this invention is used to treat benign prostatic hyperplasia (BPH) in a patient in need thereof.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with silodosin. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I and a second therapeutic agent selected from a 5-alpha reductase inhibitors (e.g., finasteride (PROSCAR®) and dutasteride (AVODART®)), HMG-CoA reductase inhibitors (e.g., atorvastatin (LIPITOR®), lovastatin (MEVACOR®), simvastatin (ZOCOR®) fluvastatin (LESCOL®), pravastatin (PRAVACHOL®) and rosuvastatin (CRESTOR®)), EGF-receptor antagonists, and beta-3-adrenoceptor antagonists for the treatment of benign prostatic hyperplasia.

In a particular embodiment, the second agent is a 5-alpha-reductase inhibitor and the subject is suffering from benign prostatic hyperplasia. In more particular embodiment, the 5-alpha-reductase inhibitor is a finasteride or dutasteride. In a most particular embodiment, the 5-alpha-reductase inhibitor is finasteride.

In an even more specific embodiment, the combination therapies of this invention include treatment of benign prostatic hyperplasia by administering a compound of Formula I, a pharmaceutically acceptable salt thereof, a composition of Formula (I) or a pharmaceutical composition of Formula (I) in combination with a 5-alpha-reductase inhibitor. In a more particular embodiment, the 5-alpha-reductase inhibitor is a finasteride or dutasteride. In a most particular embodiment, the 5-alpha-reductase inhibitor is finasteride.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

Diagnostic Methods and Kits

The compounds and compositions of this invention are also useful as reagents in methods for determining the concentration of silodosin in solution or biological sample such as plasma, examining the metabolism of silodosin and other analytical studies.

According to one embodiment, the invention provides a method of determining the concentration, in a solution or a biological sample, of silodosin, comprising the steps of:
a) adding a known concentration of a compound of Formula I to the solution of biological sample;
b) subjecting the solution or biological sample to a measuring device that distinguishes silodosin from a compound of Formula I;
c) calibrating the measuring device to correlate the detected quantity of the compound of Formula I with the known concentration of the compound of Formula I added to the biological sample or solution; and
d) measuring the quantity of silodosin in the biological sample with said calibrated measuring device; and
e) determining the concentration of silodosin in the solution of sample using the correlation between detected quantity and concentration obtained for a compound of Formula I.

Measuring devices that can distinguish silodosin from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the subject; and comparing the amount of the compound of Formula I with the metabolic products of the compound of Formula I in the serum, urine or feces sample.

The present invention also provides kits for use to treat a disease or condition selected from benign prostate hyperplasia (BPH); high intraocular pressure; high cholesterol; impotency; female sexual dysfunction (FSD) (e.g, female sexual arousal disorder (FSAD) and female orgasmic disorder (FOD)), sympathetically mediated pain; cardiac arrhythmia; and migraine. These kits comprise (a) a pharmaceutical composition comprising a compound of Formula I or a salt thereof, wherein said pharmaceutical composition is in a container; and (b) instructions describing a method of using the pharmaceutical composition to treat the particular disease or condition. In a specific embodiment, the kit is used to treat BPH.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of (R)-1-(3-hydroxypropyl)-5-(2-(2-(2-(2,2,2-d2-trifluoroethoxy)phenoxy)-d4-ethylamino)propyl)indoline-7-carboxamide 110.

Compound 110 was prepared according to the procedure outlined in Scheme 6, below.

Scheme 6. Synthesis of Compound 110.

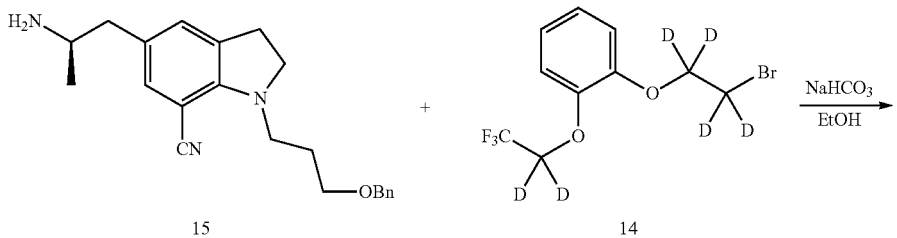

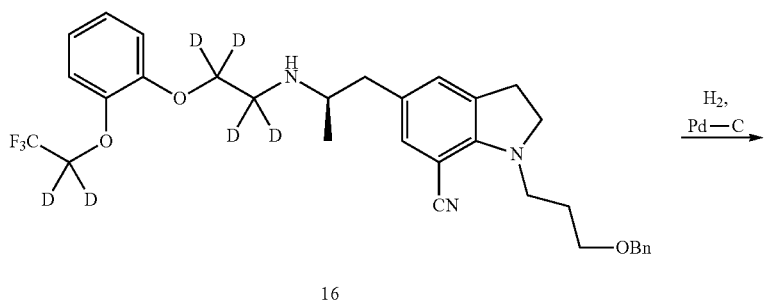

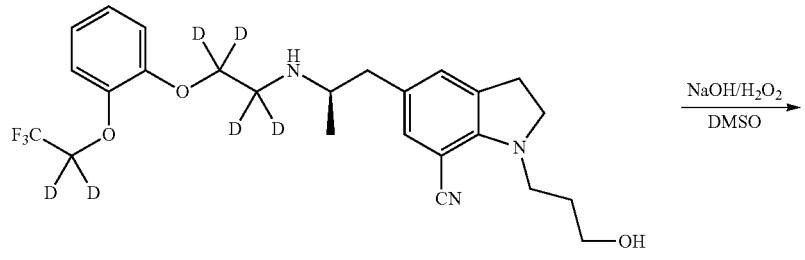

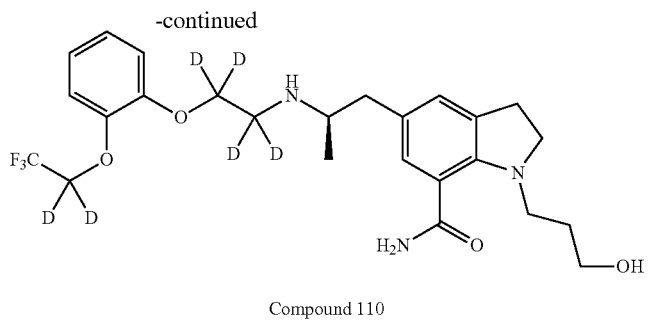

Compound 110

Synthesis of (R)-1-(3-(benzyloxy)propyl)-5-(2-(2-(2-(2,2,2-trifluoro-1-d₂-ethoxy)phenoxy)ethyl-d₄-amino)propyl)indoline-7-carbonitrile (16). Sodium bicarbonate (50 mg, 0.60 mmol) was added to a solution of bromide 14 (150 mg, 0.49 mmol) and amine 15 (200 mg, 0.57 mmol) in ethanol (1 mL). (Amine 15 starting material was prepared as outlined in Japanese patent, JP 2006188470). The mixture was heated in a sealed tube at 105° C. for 6 h then was cooled to room temperature and poured into ethyl acetate (100 mL). The resultant mixture was washed twice with water and the organic layer was dried over sodium sulfate, filtered and the filtrate concentrated under reduced pressure. The crude product was purified by column chromatography on silica gel to give 140 mg of 16 and 60 mg of bromide starting material 14. $^1$H NMR (CDCl$_3$) δ 7.25-7.35 (m, 5H), 6.85-7.1 (m, 6H), 4.49 (s, 2H), 3.59-3.7 (m, 4H), 3.5 (t, 2H), 2.83-2.95 (m, 3H), 2.53-2.65 (m, 1H), 2.38-2.45 (m, 1H), 1.9-2.0 (m, 2H), 1.05 (d, 3H). LCMS m/z=574 (M+H).

Synthesis of (R)-1-(3-hydroxypropyl)-5-(2-(2-(2-(2,2,2-trifluoro-1-d₂-ethoxy)phenoxy)ethyl-d₄-amino)propyl)indoline-7-carbonitrile (17). A mixture of benzyl ether 16 (130 mg, 0.23 mmol), Pd(OH)$_2$ (60 mg), 1M HCl (3 mL) and ethanol (4 mL) was hydrogenated at 30 psi H$_2$ for 2 h. Although reduction was not complete, LCMS showed 17 to be the predominant product. The mixture was filtered through celite, and concentrated under reduced pressure to give crude 17. LCMS m/z=484 (M+H).

Synthesis of (R)-1-(3-hydroxypropyl)-5-(2-(2-(2-(2,2,2-d2-trifluoroethoxy)phenoxy)-d4-ethylamino)propyl)indoline-7-carboxamide (Compound 110). To a solution of crude product 17 from above (30 mg) in DMSO (0.5 mL) was added 30% H$_2$O$_2$ (0.1 ml). The mixture was stirred for 10 min and 5N NaOH (0.1 mL) was added. The mixture was then stirred for 1 h at which time LCMS of the reaction mixture showed that the desired product, Compound 110, had formed as the predominant species as determined by HPLC/MS. HPLC (method: 20 mm C18-RP column—gradient method 2-95% ACN+0.1% formic acid in 3.3 min with 1.7 min hold at 95% ACN; Wavelength: 254 nm): retention time: 2.37 min. LCMS m/z=502 (M+H).

Example 2

Synthesis of 1-(2-bromo-d4-ethoxy)-2-(2,2,2-d2-trifluoroethoxy)benzene 14. Intermediate 14 was prepared according to the procedure outlined in Scheme 7 below.

Scheme 7. Synthesis of Intermediate 14.

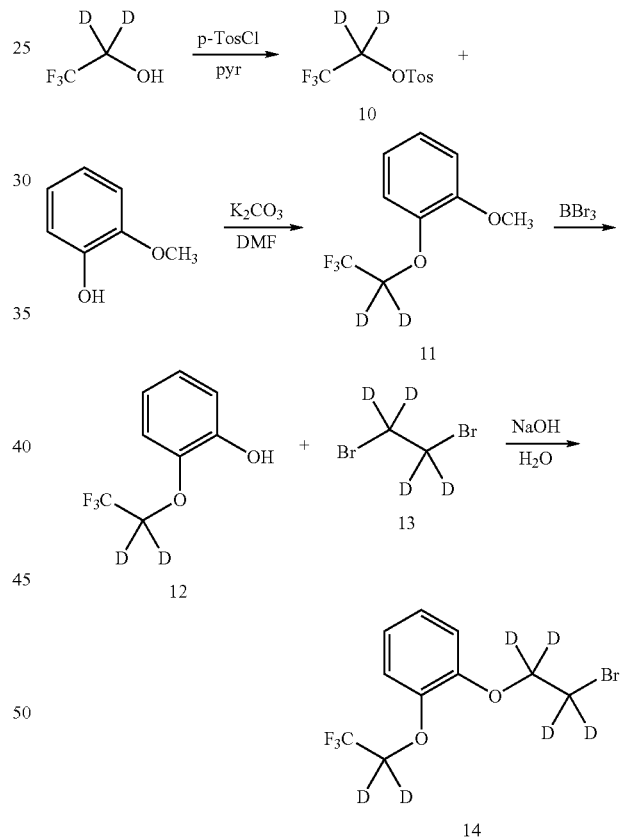

Synthesis of 2,2,2-trifluoroethanol-1-d₂-tosylate (10). A mixture of 2,2,2-trifluoroethanol-1-d₂ (4.0 g, 39.2 mmol) and p-toluenesulfonyl chloride (9.0 g, 43.6 mmol) was cooled in an ice bath and pyridine (12 mL) was added dropwise. The mixture was stirred for 4 h, poured into a separatory funnel containing ice-water, shaken, then extracted with ethyl acetate (250 mL). The organic phase was washed sequentially with 2M sulfuric acid (2×100 mL), aqueous sodium bicarbonate, brine, then dried over sodium sulfate. The mixture was filtered and the filtrate concentrated under reduced pressure. The crude product was purified by column chromatography on silica gel to give 6.8 g (68%) of 2,2,2-trifluoroethanol-1-$d_2$ tosylate 10. $^1$H NMR (CDCl$_3$) δ: 7.82 (d, 2H), 7.40 (d, 2H), 2.45 (s, 3H). LCMS m/z=257 (M+H).

Synthesis of 1-methoxy-2-(2,2,2-trifluoro-1-$d_2$-ethoxy)benzene (11). A mixture of guaiacol (1.67 g, 13.5 mmol), 2,2,2-trifluoroethanol-1-$d_2$ tosylate 10 (3.80 g, 14.8 mmol), potassium carbonate (3.70 g, 26.8 mmol) and N,N-dimethylformamide (25 mL) was heated and stirred at 140-150° C. for 4 h, then stirred at room temperature overnight. Water (200 mL) was added to the reaction mixture and the mixture extracted with 1:1 MTBE/hexanes (2×150 mL). The aqueous phase was extracted with MTBE (2×100 mL), the organic solutions combined and washed sequentially with 0.5N NaOH (100 mL), water (3×100 mL), brine, then dried over sodium sulfate. The mixture was filtered and the filtrate concentrated under reduced pressure. The crude product was purified by column chromatography on silica gel to give 2.30 g (75%) of 1-methoxy-2-(2,2,2-trifluoro-1-$d_2$-ethoxy)benzene 11 and 0.6 g of the starting tosylate 10. $^1$H NMR (CDCl$_3$) δ 7.02 (m, 2H), 6.9 (m, 2H), 3.85 (s, 3H).

Synthesis of 2-(2,2,2-trifluoro-1-$d_2$-ethoxy)phenol (12). To a solution of 1-methoxy-2-(2,2,2-trifluoro-1-$d_2$-ethoxy)benzene 11 (1.82 g, 8.74 mmol) in dichloromethane (15 mL) cooled in an ice-bath was added boron tribromide (1.8 mL). The resultant solution was stirred for 0.5 h, ice was added and the mixture was stirred for 10 min. The mixture was transferred to a separatory funnel and extracted with ethyl acetate (200 mL). The organic phase was washed with water, aqueous sodium bicarbonate, brine, and dried over sodium sulfate. The mixture was filtered and the filtrate concentrated under reduced pressure. The crude product was passed through a short silica gel column to give 1.44 g of 12. $^1$H NMR (CDCl$_3$) δ 6.96 (m, 2H), 6.85 (m, 2H), 5.52 (s, 1H). LCMS did not show a molecular ion.

Synthesis of 1-(2-bromoethoxy-$d_4$)-2-(2,2,2-trifluoro-1-$d_2$-ethoxy)benzene (14). A mixture of alcohol 12 (1.2 g, 6.18 mmol), 1,2-dibromoethane-$d_4$ 13 (0.8 mL), NaOH (0.27 g, 6.75 mmol) and water (10 mL) was heated at 120° C. for 10 h. After cooling to room temperature the mixture was diluted with water (30 mL), the aqueous phase was extracted with ethyl acetate (300 mL), and the organic phase was washed with 1M HCl, brine, and dried over sodium sulfate. The mixture was filtered and the filtrate concentrated under reduced pressure. The crude product was purified by column chromatography on silica gel to give 960 mg of 14. $^1$H NMR (CDCl$_3$) δ 7.03 (m, 2H), 6.95 (m, 2H). LCMS m/z=304 (M+H).

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., XenoTech, LLC (Lenexa, Kans.)). The incubation mixtures are prepared as follows:

| Reaction Mixture Composition | |
| --- | --- |
| Liver Microsomes | 0.5-2.0 mg/mL |
| NADPH | 1 mM |
| Potassium Phosphate, pH 7.4 | 100 mM |
| Magnesium Chloride | 10 mM |
| Test Compound | 0.1-1 µM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH$_2$O to terminate the reaction. The positive controls, testosterone and propranolol, as well as silodosin, are each run simultaneously with the test compounds in separate reactions. All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 µM of a compound of test compound in 100 mM potassium phosphate buffer (pH 7.4) is incubated at 37° C. in triplicate. Positive controls contain 1 µM of silodosin instead of test compound. Negative controls used Control Insect Cell Cytosol (insect cell microsomes that lacked any human metabolic enzyme) purchased from GenTest (Woburn, Mass., USA). Aliquots (50 µL) are removed from each sample and placed in wells of a multi-well plate at various time points (e.g., 0, 2, 5, 7, 12, 20, and 30 minutes) and to each aliquot is added 50 µL of ice cold acetonitrile with 3 µM haloperidol as an internal standard to stop the reaction.

Plates containing the removed aliquots are placed in −20° C. freezer for 15 minutes to cool. After cooling, 100 µL of deionized water is added to all wells in the plate. Plates are then spun in the centrifuge for 10 minutes at 3000 rpm. A portion of the supernatant (100 µL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordi-

What is claimed is:

1. A compound of Formula I:

[Chemical structure of Formula I showing a molecule with F₃C-O-phenyl-O-C(R⁵ᵃR⁵ᵇ)-C(R⁴ᵃR⁴ᵇ)-NH-CH(CH₃)-CH₂- connected to an indoline ring system with H₂N-C(=O) group, and various R groups labeled R¹ᵃ, R¹ᵇ, R²ᵃ, R²ᵇ, R³ᵃ, R³ᵇ, R⁴ᵃ, R⁴ᵇ, R⁵ᵃ, R⁵ᵇ, R⁶ᵃ, R⁶ᵇ, R⁷ᵃ, R⁷ᵇ, R⁸ᵃ, R⁸ᵇ, with an HO group]

or a pharmaceutically acceptable salt thereof, wherein:
each R is independently selected from hydrogen or deuterium; and
at least one R is deuterium;
each deuterium present at a site designated as a site of deuteration is present at an isotopic enrichment of at least 500; and
wherein (a) $R^{4a}$ and $R^{4b}$ are simultaneously deuterium (b) $R^{4a}$ and $R^{5b}$ are simultaneously deuterium and (c) $R^{6a}$ and $R^{6b}$ are simultaneously deuterium.

2. The compound of claim 1, wherein each pair of R groups bound to a common carbon atom is the same, and is selected independently from any other pair of R groups.

3. The compound of claim 1, wherein $R^{7a}$, $R^{7b}$, $R^{8a}$ and $R^{8b}$ are the same.

4. The compound of claim 3, wherein $R^{7a}$, $R^{7b}$, $R^{7a}$ and $R^{8b}$ are simultaneously deuterium.

5. The compound of claim 1, wherein $R^{1a}$, $R^{1b}$, $R^{2a}$, $R^{2b}$, $R^{3a}$, and $R^{3b}$ are simultaneously deuterium.

6. The compound of claim 2 selected from any one of the compounds set forth in the table below:

| Cmpd | each R¹ | each R² | each R³ | each R⁴ | each R⁵ | each R⁶ | each R⁷ | each R⁸ |
|---|---|---|---|---|---|---|---|---|
| 100 | D | D | D | D | D | D | D | D |
| 108 | D | D | D | D | D | D | H | H |
| 110 | H | H | H | D | D | D | H | H | or a pharmaceutically acceptable salt thereof.

7. A pyrogen-free composition comprising a compound according to claim 1 or a pharmaceutically acceptable salt thereof and an acceptable carrier.

8. The composition according to claim 7, wherein the composition is suitable for pharmaceutical use and said carrier is a pharmaceutically acceptable carrier.

9. The composition according to claim 8, further comprising a second therapeutic agent selected from a 5-alpha reductase inhibitors, an HMG-CoA reductase inhibitor, an EGF-receptor antagonist and a beta-3-adrenoceptor antagonist.

10. The composition of claim 9, wherein the second therapeutic agents is finasteride or dutasteride.

11. A method of increasing the activity of an alpha (1A)-adrenoceptor in a cell, comprising the step of contacting the cell with a compound according to claim 1 or a pharmaceutically acceptable salt thereof.

12. A method of treating benign prostate hyperplasia (BPH) in a patient in need thereof comprising the step of administering to the patient a compound according to claim 1 or a pharmaceutically acceptable salt thereof.

13. The method of claim 12, comprising the additional step of co-administering to the patient in need thereof a second therapeutic agent selected from a 5-alpha reductase inhibitors, an HMG-CoA reductase inhibitor, an EGF-receptor antagonist and a beta-3-adrenoceptor antagonist.

14. The method of claim 13, wherein the second therapeutic agents is finasteride or dutasteride.

15. The compound of claim 2, wherein $R^{7a}$, $R^{7b}$, $R^{8a}$ and $R^{8b}$ are the same.

16. The compound of claim 15, wherein $R^{7a}$, $R^{7b}$, $R^{8a}$ and $R^{8b}$ are simultaneously deuterium.

17. The compound of claim 2, wherein $R^{1a}$, $R^{1b}$, $R^{2a}$, $R^{2b}$, $R^{3a}$, and $R^{3b}$ are simultaneously deuterium.

18. The composition of claim 8, wherein each pair of R groups bound to a common carbon atom is the same, and is selected independently from any other pair of R groups.

19. The composition of claim 8, wherein $R^{7a}$, $R^{7b}$, $R^{8a}$ and $R^{8b}$ are the same.

20. The composition of claim 19, wherein $R^{7a}$, $R^{7b}$, $R^{8a}$ and $R^{8b}$ are simultaneously deuterium.

21. The composition of claim 8, wherein $R^{1a}$, $R^{1b}$, $R^{2a}$, $R^{2b}$, $R^{3a}$, and $R^{3b}$ are simultaneously deuterium.

22. The composition of claim 18 wherein the compound is selected from any one of the compounds set forth in the table below:

| Cmpd | each R¹ | each R² | each R³ | each R⁴ | each R⁵ | each R⁶ | each R⁷ | each R⁸ |
|---|---|---|---|---|---|---|---|---|
| 100 | D | D | D | D | D | D | D | D |
| 108 | D | D | D | D | D | D | H | H |
| 110 | H | H | H | D | D | D | H | H | or a pharmaceutically acceptable salt thereof.

23. The composition of claim 18, wherein any atom not designated as deuterium is present at its natural isotopic abundance.

24. The method of claim 12, wherein each pair of R groups bound to a common carbon atom is the same, and is selected independently from any other pair of R groups.

25. The method of claim 12, wherein $R^{7a}$, $R^{7b}$, $R^{8a}$ and $R^{8b}$ are the same.

26. The method of claim 25, wherein $R^{7a}$, $R^{7b}$, $R^{8a}$ and $R^{8b}$ are simultaneously deuterium.

27. The method of claim 12, wherein $R^{1a}$, $R^{1b}$, $R^{2a}$, $R^{2b}$, $R^{3a}$, and $R^{3b}$ are simultaneously deuterium.

28. The method of claim 24 wherein the compound is selected from any one of the compounds set forth in the table below:

| Cmpd | each $R^1$ | each $R^2$ | each $R^3$ | each $R^4$ | each $R^5$ | each $R^6$ | each $R^7$ | each $R^8$ |
|------|------|------|------|------|------|------|------|------|
| 100 | D | D | D | D | D | D | D | D |
| 108 | D | D | D | D | D | D | H | H |
| 110 | H | H | H | D | D | D | H | H | or a pharmaceutically acceptable salt thereof.

29. The method of claim 24, wherein any atom not designated as deuterium is present at its natural isotopic abundance.

30. The compound of any one of claims 1, 2, 3-6 or 15-17, wherein any atom not designated as deuterium is present at its natural isotopic abundance.

* * * * *

UNITED STATES PATENT AND TRADEMARK OFFICE
CERTIFICATE OF CORRECTION

PATENT NO. : 8,013,007 B2
APPLICATION NO. : 12/072501
DATED : September 6, 2011
INVENTOR(S) : Julie F. Liu It is certified that error appears in the above-identified patent and that said Letters Patent is hereby corrected as shown below:

| | |
|---|---|
| Col. 31, Line 32 | Replace "$R^{4a}$ and $R^{5b}$" with "$R^{5a}$ and $R^{5b}$" |
| Col. 31, Line 40 | Replace "$R^{7a}$, $R^{7b}$, $R^{7a}$ and $R^{8a}$" with "$R^{7a}$, $R^{7b}$, $R^{8a}$ and $R^{8b}$" |
| Col. 31, Line 66 | Replace "inhibitors" with "inhibitor" |
| Col. 32, Line 2 | Replace "agents" with "agent" |
| Col. 32, Lines 14-15 | Replace "inhibitors" with "inhibitor" |
| Col. 32, Line 19 | Replace "agents" with "agent" |

Signed and Sealed this
Thirty-first Day of January, 2012

David J. Kappos
*Director of the United States Patent and Trademark Office*